United States Patent [19]

Dennis et al.

[11] Patent Number: 5,464,754
[45] Date of Patent: Nov. 7, 1995

[54] ASSAY AND SUBSTRATE FOR ARACHIDONOYL-SPECIFIC PHOSPHOLIPASE A2

[75] Inventors: Edward A. Dennis, La Jolla; Laure J. Reynolds; Lin Yu, both of San Diego, all of Calif.

[73] Assignee: The Regents of the University of California, Oakland, Calif.

[21] Appl. No.: 107,378

[22] Filed: Aug. 17, 1993

[51] Int. Cl.$^6$ .............................. C12Q 1/34; C12P 21/06; C07C 321/00; A01N 57/36
[52] U.S. Cl. .............................. 435/18; 435/69.2; 435/19; 435/20; 435/11; 560/152; 514/103; 514/86; 514/126
[58] Field of Search .............................. 435/18, 69.2, 19, 435/20, 11; 560/152; 514/103, 86, 126

[56] References Cited

U.S. PATENT DOCUMENTS

| | | | |
|---|---|---|---|
| 4,649,215 | 3/1987 | von Sprecher et al. | 560/152 |
| 4,959,357 | 9/1990 | Reers et al. | 514/103 |
| 5,124,334 | 6/1992 | Wilkerson | 514/277 |
| 5,144,045 | 9/1992 | Wissner et al. | 514/103 |

FOREIGN PATENT DOCUMENTS

| | | |
|---|---|---|
| 01231896 | 9/1989 | Japan. |
| 91035544 | 3/1991 | WIPO. |
| 9222289 | 12/1992 | WIPO. |

OTHER PUBLICATIONS

Bhatia et al (Abstract); "Synthesis", (1), 16p, 1989.

Nichols, et al., "Adenosine triphosphate-sensitive potassium channels in the cardiovascular system", *Am J. Physiol.*, 30(6):H1675-H1686 (1991).

Rosario, et al., "Membrane Potential Measurements in Islets of Langerhans from ob/ob Obese Mice Suggest an Alteration in [Ca$^{2+}$]; -Activated K$^+$Permeability", *Quarterly Journal of Experimental Physiology*, 70(1):137-150 (1985).

Kubo, et al., "Primary structure and functional expression of a mouse inward rectifier potassium channel", *Nature*, 362:127-133 (1993).

Trautwein, et al., "Zum Mechanismus der Membranwirkung des Acetylcholin an der Herzmuskelfaser", *Pflëgers Archiv*, 266:324-334 (1958).

Clark, et al., "A Novel Arachidonic Acid-Selective Cytosolic PLA$_2$ Contains a Ca$^{2+}$-Dependent Translocation Domain with Homology to PKC and GAP", *Cell*, 65:1043-1051 (1991).

Sharp, et al., "Molecular Cloning and Expression of Human Ga$^{2+}$-sensitive Cytosolic Phospholipase A$_2$*", *The Journal of Biological Chemistry*, 266(23):14850-14853 (1991).

Wijkander, et al., "Macrophage Arachidonate-Mobilizing Phospholipase A$_2$: Role of Ca$^{2+}$ for Membrane Binding but Not for Catalytic Activity", *Biochemical and Biophysical Research Communication*, 184(1):118-124 (1992).

Ghomashchi, et al., "Kinetic Analysis of a High Molecular Weight Phospholipase A$_2$ from Rat Kidney: Divalent Metal-Dependent Trapping of Enzyme on Product-Containing Vesicles", *Biochemistry*, 31:3814-3824 (1992).

(List continued on next page.)

*Primary Examiner*—Michael G. Wityshyn
*Assistant Examiner*—Louise N. Leary
*Attorney, Agent, or Firm*—Walter H. Dreger; Jan P. Brunelle

[57] ABSTRACT

A non-radioactive, spectrophotometric, microtiter plate assay for human cystolic phospholipase A$_2$ (cPLA$_2$) is described. The assay utilizes a novel synthetic thiol-phospholipid analog as a substrate. In one embodiment, the substrate is a phosphatidylcholine derivative with an arachidonoylthioester in the sn-2 position and an alkenyl-ether or alkenyl-ether in the sn-1 position. The alkyl-ether and the alkenyl-ether in the sn-1 position of the substrate ensures that the assay will only measure cPLA$_2$ activity and will not be complicated by metabolism of the lysophospholipid product by the enzyme's and lysopholypase activity.

23 Claims, 2 Drawing Sheets

OTHER PUBLICATIONS

Reynolds, et al., "Metal ion and salt effects on the phospholipase $A_2$, lysophospholipase, and transacylase activities of human cytosolic phospholipase $A_2$", *Biochemica et Biophysica Acta*, 1167:272–280 (1993).

Ibrahim, "The Contaminating Effects of Cephalins in Estimating Non–Esterified Fatty Acids", *Biochim. Biophys. Acta*, 137:413–419 (1967).

Bligh, et al., "A Rapid Method fo Total Lipid Extraction and Purification", *Can. J. Biochem. Physiol.*, 37(8):911–917 (1959).

Reynolds, et al., "Analysis of Human Synovial Fluid Phospholipase $A_2$ on Short Chain Phosphatidylcholine–Mixed Micelles: Development of a Spectrophotometric Assay Suitable for a Microtiterplate Reader", *Analytical Biochemistry*, 204:190–197 (1992).

Miyashita, et al., "Pyridinium–Toluenesulfonate. A Mild and Efficient Catalyst for the Tetrahydropyranylation of Alcohols", *J. Org. Chem.*, 42(23):3772–3774 (1977).

Kramer, et al., "The $Ca^{2+}$–sensitive Cytosolic Phospholipase $A_2$ Is a 100–kDa Protein in Human Monoblast U937 Cells", *The Journal of Biological Chemistry*, 266(8):5268–5272 (1991).

Clark et al., "Purification of a 110–kilodalton cytosolic phospholipase $A_2$ from the human monocytic cell line U937" *Proc. Natl. Acad. Sci. USA*, 87:7708–7712 (1990).

Leslie, "Kinetic Properties of a High Molecular Mass Arachidonoyl–hydrolyzing Phospholipase $A_2$ That Exhibits Lysophospholipase Activity", *The Journal of Biological Chemistry*, 266(17):11366–11371 (1991).

Ulevitch, et al., "Solubilization, Purification, and Characterization of a Membrane–bound Phospholipase $A_2$ from the P388$D_1$ Macrophage–like Cell Line", *The Journal of Biological Chemistry*, 263(7):3079–3985 (1988).

Diez, et al., "Substrate Specificities and Properties of Human Phospholipases $A_2$ in a Mixed Vesicle Model", The Journal of Biological Chemistry, 267(26):18342–18348 (1992).

Ryu, et al., "Modification of the Dittmer–Lester reagent for the detection of phospholipid derivatives on thin–layer chromatograms", *Journal of Lipid Research*, 20:561–563 (1979).

Brockerhoff, et al., "Improved Synthesis of Choline Phospholipids", *Lipids*, 14(1):88–89 (1978).

Dennis, "Phospholipases", *Methods in Enzymology*, 197:63–75 (1991).

Hendrickson, et al., "Kinetic Analysis of the Dual Phospholipid Model for Phospholipase $A_2$ Action", *The Journal of Biological Chemistry*, 259(9):5734–5739 (1984).

Dennis, "Phospholipases", *The Enzymes*, XVI:305–353 (1983).

Mayer, et al., "New insights on mammaliah phospholipase $A_2$(s); comparison of arachidonoyl–selective and –nonselective enzymes", *The FASEB Journal*, 7:339–348 (1993).

Dennis, "Phospholipase $A_2$ Activity Towards Phosphatidylcholine in Mixed Micelles: Surface Dilution Kinetics and the Effect of Thermotropic Phase Transitions" *Arc. of Biochem. and Biophys.* 158 485–493 (1973).

Yu, et al., *Methods in Enzymology*, 197 pp. 65–76 (1991) "Thio–Based Phospholipase Assay".

Bhatia et al., *Synthesis*, 1 pp. 16–20 (1989) "Stereospecific Synthesis of 2–Substituted Ether Phospholipids".

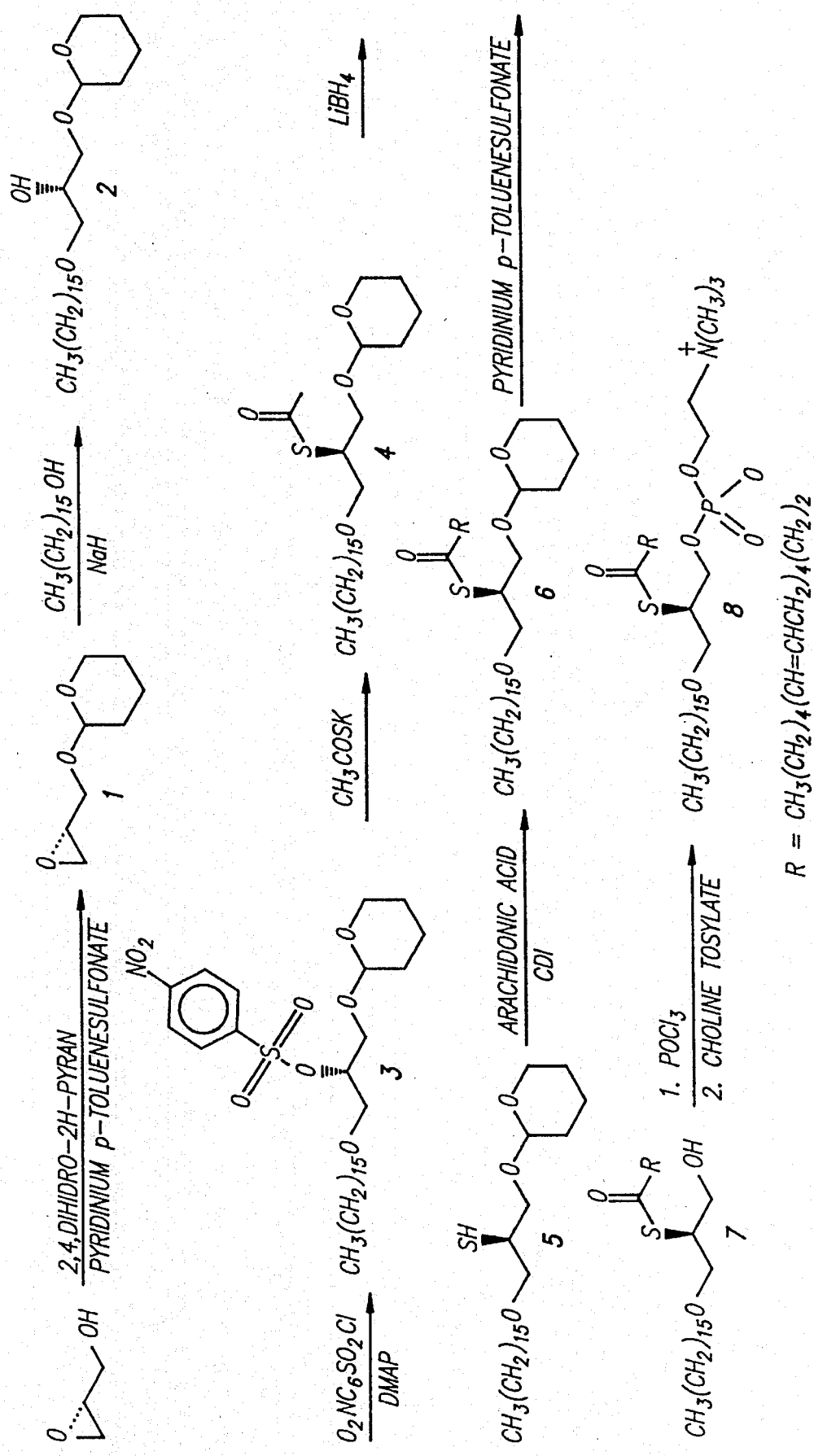
FIG._1

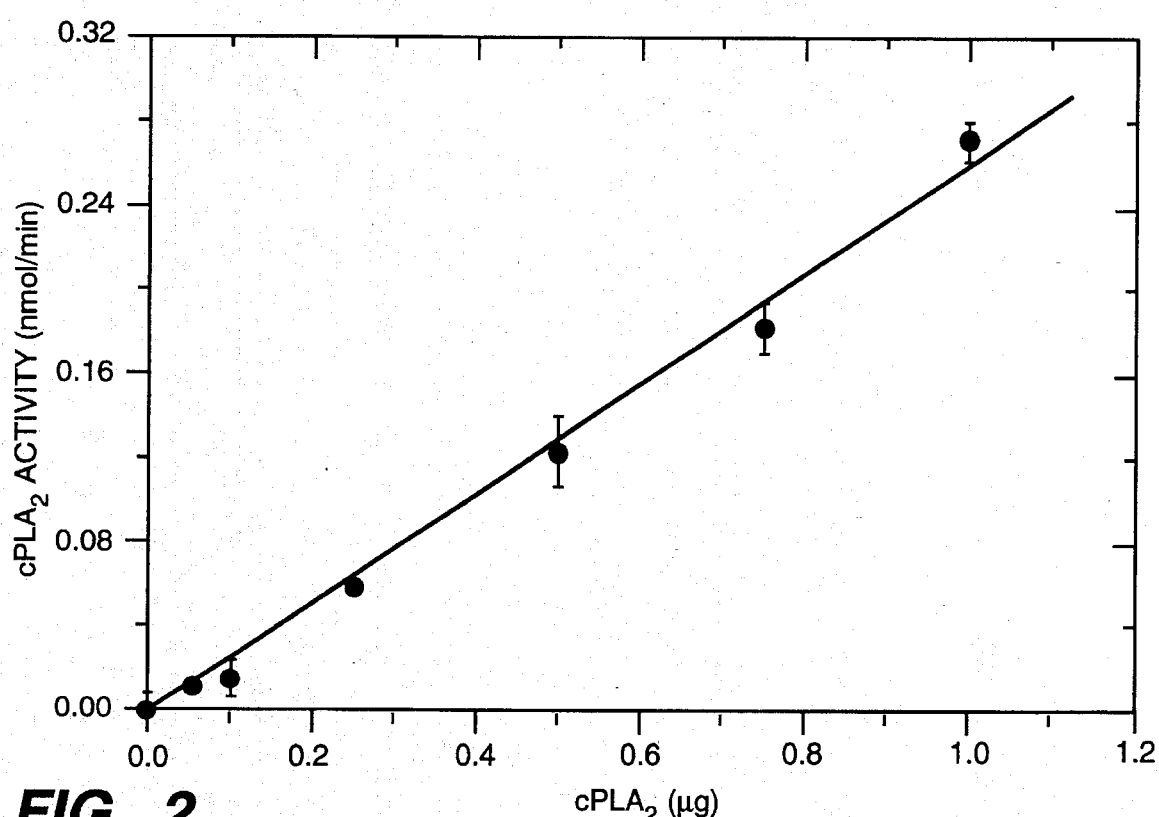
FIG._2
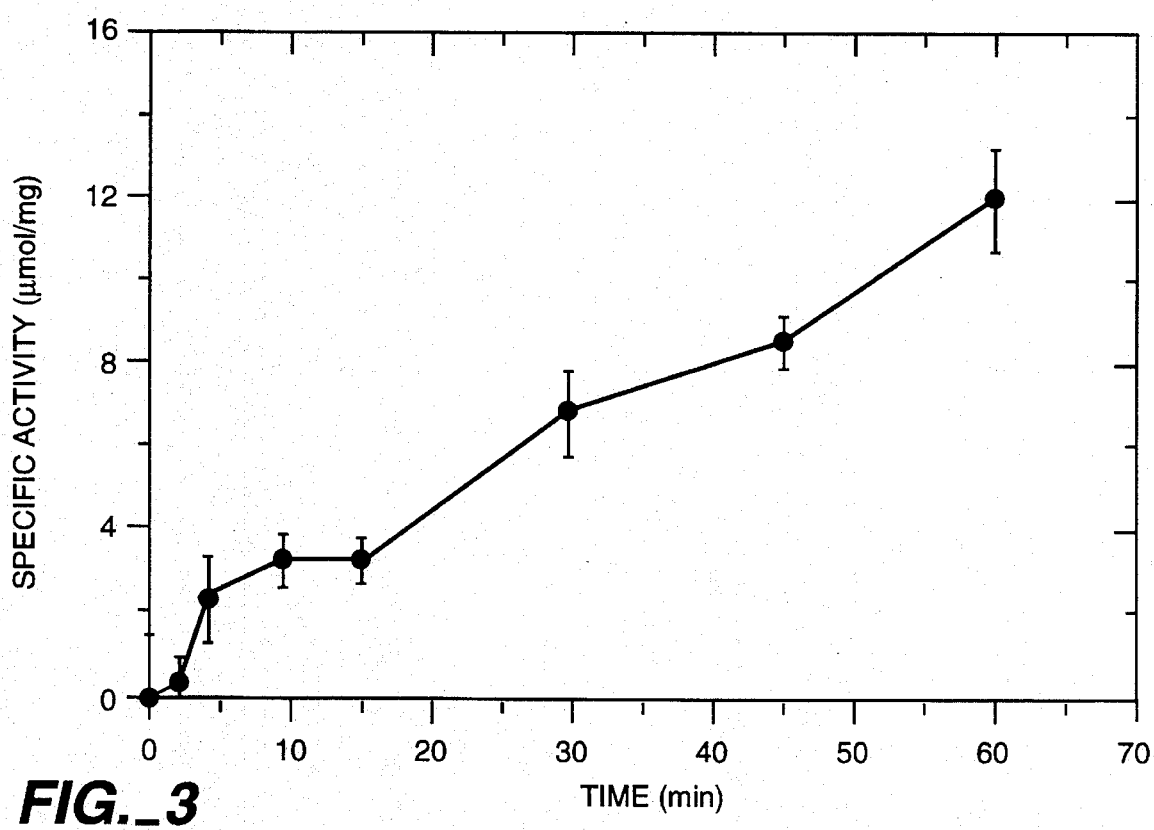
FIG._3

ASSAY AND SUBSTRATE FOR ARACHIDONOYL-SPECIFIC PHOSPHOLIPASE A2

BACKGROUND OF THE INVENTION

Human cystolic phospholipase $A_2$ (cPLA) is an arachidonic acid specific enzyme which is of considerable interest due to its proposed roles in arachidonic acid release, eicosanoid production, and signal transduction.

This enzyme bears little resemblance to the more well-studied extracellular or secretory phospholipase $A_2$ enzymes (sPLA) obtained from snake or bee venom, mammalian pancreas, or human synovial fluid. The sPLA's are small, 14 kDa proteins which are dependent on $Ca^{2+}$ for catalytic activity.

The cPLA enzyme is an 85 kDa protein which is also activated by $Ca^{2+}$(Clark et al. *Cell* 65:1043–1051 (1991) and Sharp et al., *J. Biol. Chem.* 266:14850–14853 (1991)). However, rather than playing a catalytic role, the $Ca^{2+}$ appears to be required for binding of the enzyme to the membrane substrate (Clark et al. supra; Wijkander et al., *Biochem. Biophys. Res. Comm.* 184:118–124 (1992); Ghomashchi et al., *Biochemistry* 31:3814–3824 (1992); and Reynolds, et al., *Biochim. Biophys. Acta* 1167:272–280 (1993)). Another difference between the enzymes is that the sPLA's catalyze only the phospholipase $A_2$ reaction while cPLA is non-specific and displays lysophospholipase and transacylase activities as well as phospholipase $A_2$ activity (Reynolds, et al., supra).

Because of the potential role of this enzyme in eicosanoid production, there is considerable interest in developing pharmacologically effective inhibitors of cPLA as anti-inflammatory agents. Accordingly, assays that are capable of detecting cPLA are necessary for designing inhibitors of the enzyme.

The assays currently utilized for the measurement of cPLA enzyme are radioactive assays which involve organic extraction of lipids, usually by either the methods of Dole, (Ibrahim, S. S. *Biochim. Biophys. Acta* 137:413–419 (1967)); or Bligh and Dyer, (*Can. J. Biochem. Biophysiol.* 37:911–917 (1959)); followed by either a silica column or TLC separation.

These radioactive assays utilize a variety of substrate forms including pure sonicated phospholipid vesicles, (Ghomashchi et al., supra; and Leslie, C. C. *J. Biol. Chem.* 266:11366–11371 (1991)); sonicated phospholipid/dioleoylglycerol (DAG) mixtures, (Kramer, R. M., et al. *J. Biol. Chem.* 266:5268–5272 (1991)); and mixed micelles of phospholipid/Triton X-100 with glycerol, (Clark, J. D., et al. *Proc. Natl. Acad. Sci.* 87:7708–7712 (1990), and Ulevitch, R. J. et al. *J. Biol. Chem.* 263:3079–3085 (1988)). These radioactive assays are generally tedious and difficult to use in routine screening programs. They also each have particular drawbacks. Most notable is a non-linear time course observed in vesicle assays, where the activity plateaus and stops after only a few minutes. The DAG assay, while not linear, has a somewhat better time course, but is typically run at a very low substrate concentrations where the interpretation of inhibition data can be difficult. The Triton/glycerol assays have the best time course, but require a considerable amount of enzyme.

Accordingly, it is an object of this invention to provide a novel substrate for cPLA that can be used in a spectrophotometric assay. It is a further object of this invention to provide a rapid, convenient, and reliable assay for cPLA that exhibits a linear time course. Additional objects and features of the invention will be apparent to those skilled in the art from the following detailed description and appended claims when taken in conjunction with the figures.

SUMMARY OF THE INVENTION

A synthetic substrate for cytosolic phospholipase $A_2$ (cPLA) is described. The substrate is an analogue of naturally occurring phospholipids and comprises a glycerol backbone having an alkenyl-ether in the sn-1 position, an unsaturated alkenylthioester at the sn-2 position, and a phosphate linked to a polar group at the sn-3 position.

The novel substrates of the present invention are represented by the formula:

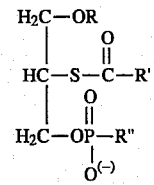

wherein R is an alkyl or alkenyl group having from about 6 to about 18 carbon atoms, R' is an alkenyl group having at least one double bond and having from about 16 to about 22 carbon atoms, and R" is a polar group comprising groups selected from the group consisting of oxy radicals of choline, ethanolamine, inositol, serine, glycerol, and alkanols having from 1 to 4 carbons.

Preferred among these substrates are those wherein R' is the alkenyl component of an arachidonic acid and wherein R" is an oxy radical of an alcohol selected from the group consisting of choline, ethanolamine, inositol, serine, and glycerol. Further preferred are those thereof wherein R is hexadecyl and R" is an oxy radical of choline.

It will be appreciated that the novel substrates hereof are uniquely useful by virtue of being arachidonic-acid specific. Thus, consistent with that feature it will be appreciated that bioequivalent molecules represented both by the literal definitions of the substrates hereof and equivalent species falling within the interpretational ambit thereof are included within the scope of this invention.

A method for the detection of cPLA activity is also described wherein a solution of the novel substrate of the present invention is incubated with cPLA to allow hydrolysis of the substrate by cPLA. The hydrolysis produces a free thio-lysophospholipid. The free thiol on the lysophospholipid is then available to react with a thiol-sensitive reagent to produce a chromophore. The absorbance of the chromophore is measured using spectrophotometric means.

A method is also disclosed for measuring the effectiveness of a phospholipase $A_2$ enzyme inhibitor wherein an enzyme inhibitor is added to a substrate solution prior to the addition of cPLA. A decrease in absorbance reading compared to when no inhibitor is added indicates inhibition of the phospholipase $A_2$ activity.

BRIEF DESCRIPTION OF THE DRAWING

FIG. 1. shows the 8 steps used to synthesize 1-Hexadecyl-2-archidonoylthio-2deoxy-sn-glycero-3-phosphorylcholine from (R)-glycidol, as a model of the invention.

FIG. 2. shows the linear increase in specific activity of cytosolic phospholipase $A_2$ enzyme with increasing enzyme concentrations in the range of 0.05–1.0 µg.

FIG. 3. shows enzyme activity as a function of time.

DETAILED DESCRIPTION OF THE INVENTION

All documents referred to herein are hereby expressly incorporated by reference.

Naturally occurring phospholipids have oxy-ester linkages to long chain fatty acids at the sn-1 and sn-2 positions. The fatty acids at the sn-1 position are generally saturated with 16 to 20 carbons. The most common are palmitic and stearic acids. The fatty acids at the sn-2 position are usually unsaturated chains having 1 to 4 vinyl bonds, such as oleic, linoleic, linolenic, and arachidonic acids. Phospholipase $A_2$ activity of human cPLA displays a marked preference for phospholipid substrates with arachidonic acid in the sn-2 position. Located at the sn-3 position are a phosphate linked to a polar group. The naturally occurring polar groups are choline, ethanolamine, serine, inositol, and glycerol.

The substrates of the present invention have fatty acid derivatives at the sn-1 and sn-2 positions. The fatty acid derivatives at the sn-2 position have at least one double bond and between 18 and 22 carbons. The preferred fatty acid derivative at this position is a derivative of arachidonic acid because this is most readily recognized by cPLA. The fatty acid derivatives at the sn-2 position are linked to the glycerol backbone via a thio-ester rather than an oxy-ester linkage. Thus the substrates of the present invention are hereinafter referred to as "thiosubstrates".

Because cPLA exhibits high lysophospholipase activity in addition to the phospholipase $A_2$ activity (Reynolds et al., supra), it is preferable to synthesize a thiosubstrate for use in a cPLA assay that does not, upon reaction with cPLA, result in a further substrate for lysophospholipase activity as this will create an additional variable, making the measurement of cPLA activity more difficult. It has been found that cPLA can utilize 1-alkyl ether substrates as well as 1-acyl substrates. Advantageously, with an ether phospholipid substrate, any ether-lysophospholipid produced as a product cannot be a substrate for the lysophospholipase activity of the enzyme. Thus, only phospholipase $A_2$ activity will be measured and the assay will not be complicated by the enzymatic hydrolysis of the lysophospholipid product.

At the sn-3 position of the thiosubstrate is a phosphorus atom of a phosphate moiety linked to a polar group comprising oxy radicals of alcohols. Preferred alcohols are selected from the group consisting of the naturally occurring alcohols of phospholipids: choline, ethanolamine, glycerol, inositol, and serine. Also preferred are the alkanols having from 1 to 4 carbons: methanol, ethanol, propanol, isopropanol, and the butanols. The term "oxy radical of an alcohol" as used herein refers to an alcohol having a deprotonated hydroxyl group so that the oxygen binds to the phosphorus at the sn-3 position of the substrate. Thus, in the case of "oxy radical" of "choline" it is meant trimethylaminoethoxy depicted as $(CH_3)_3NCH_2CH_2O-$; an "oxy radical" of a butanol would include t-butyloxy or $(CH_3)_3CO-$.

Upon hydrolysis of the thiosubstrate by cPLA, a free fatty acid and a thio-lysophospholipid are produced. The free thiol on the lysophospholipid is then available to react with a thiol-sensitive reagent to produce a chromophore. As used herein, the term "thiol-sensitive reagent" refers to any compound capable of releasing a chromophore in the presence of free thiol groups.

Thiosubstrates can be synthesized using methods known in the art. One exemplified thiosubstrate is the model phosphatidylcholine derivative, 1-hexadecyl-2-arachidonoylthio-2-deoxy-sn-glycero-3-phosphorylcholine, hereinafter referred to as thioPC. This substrate can be prepared using the methods described in Example 1 below.

The methods of the present invention, for measuring the activity of cPLA, comprise adding cPLA enzyme to a thiosubstrate, incubating the reactants, and quenching the reaction by the addition of a quenching reagent and a thiol-sensitive reagent to produce a chromophore.

The substrate diluent generally comprises any suitable assay buffer system, such as HEPES, Tris-HCL, Tris-maleate, glycine, or the like. Enzyme activity increases when glycerol is a component of the substrate diluent. A suitable diluent comprises about 25%–50% glycerol, and preferably about 30% glycerol. While the enzyme activity is increased in diluents having about 70% glycerol, the diluent becomes too viscous and inhibits the mixing of solutions.

The thiosubstrate diluent also comprises an amount of detergent sufficient to solubilize! the substrate. One suitable detergent is Triton-X 100. Triton-X 100 is preferably used at concentrations of about 1–5 mM with about 1–3 mM thiosubstrate. While the highest specific activities of cPLA are observed at or below the critical micelle concentration of Triton X-100 (0.24 mM), the activity of the enzyme is more stable if the Triton X-100 is used at concentrations in the preferred range.

The detergent/glycerol diluent is preferably at pH 7.4 to approximate physiological pH and to reduce the background hydrolysis rate, although the cPLA enzyme shows greater activity at higher pH. $Ca^{2+}$ is also a component in the diluent and activates the enzyme at µM levels. However, enzyme activity continues to increase with increasing $Ca^{2+}$ concentrations, up to the mM range. The $Ca^{2+}$ can be provided by the addition of $CaCl_2$ to the diluent, preferably at concentrations greater than 1 mM, and more preferably at a concentration of about 10 mM.

The substrate/diluent solution can be combined with the cPLA enzyme in a vessel that can be used for a subsequent spectrophotometric reading, such as a cuvette, test tube, or microtiter-plate well. Enzyme activity is linear with protein concentrations in the range of about 0.05 and 1 µg of enzyme (FIG. 2).

It has been found that cPLA loses enzymatic activity in the presence of thiol-sensitive reagents, thus the assay must be run as a discontinuous endpoint assay, rather than as a continuous assay as was used previously with the sPLA enzymes (Yu et al. *Methods Enzymol.* 197:65–75 (1991); Reynolds et al. *Anal. Biochem.* 204:190–197 (1992)). The sPLA enzymes are very stable, containing 7 disulfide bonds. Because these enzymes contain no free sulfhydryl groups, the presence of thiol-sensitive reagents in the assay does not affect the enzyme and assays can be run continuously. In contrast, cPLA is an intracellular enzyme and assays and purifications are often run in the presence of reduced thiols, such as 2-mercaptoethanol or dithiothreitol (Kramer et al., supra; Clark, J. D., et al., supra). However, studies have shown a sensitivity of the cPLA enzyme to the presence of heavy metals, suggesting the presence of an important free thiol in the enzyme (Reynolds, et al., supra). Thus upon testing the sensitivity of the cPLA enzyme in the presence of the thiol-sensitive reagent 5,5'-dithiobis(2-nitrobenzoic acid) (DTNB, Ellman's reagent) it was found that enzymatic activity was lost.

After an incubation period, the enzyme/substrate reaction is quenched by the addition of a quenching reagent and a thiol-sensitive reagent. As used herein, the term "quenching reagent" refers to any compound capable of stopping the enzymatic activity of phospholipase $A_2$ enzyme. Suitable quenching reagents are $Ca^{2+}$ chelators such as ethylene glycol bis(oxyethylenenitrilo) tetraacetic acid (EGTA) and the like, or high concentrations of a detergent such as 30 mM Triton X-100. The thiol-sensitive reagent can be any reagent capable of releasing a chromophore such as DTNB or 4,4'-dithiodipyridine (DTP). DTNB is a preferred thiol-sensitive reagent because its chromophore can be detected at 405 nM, which is available to most microtiterplate readers. Although thiol-sensitive reagents inhibit cPLA enzyme activity, they do not provide a complete quench and must be used in conjunction with an additional quenching reagent such as EGTA.

After quenching and mixing, approximately one to two minutes is required for the stabilization of color development. Absorbance readings are thus made approximately three minutes after quenching to allow ample time for color stabilization. If DTNB is used as the thiol-sensitive reagent, absorbance can be measured using a dual wavelength option (405 nm–620 nm) on some microtiterplate readers to correct for light scattering.

The effectiveness of a phospholipase $A_2$ enzyme inhibitor can be measured by adding the inhibitor to the substrate solution prior to the incubation with enzyme. Enzyme activity is unaffected by DMSO at a DMSO:enzyme/substrate ratio of about 1:20. Therefore, approximately 10 μl inhibitor dissolved in DMSO can be added to 200 μl substrate solution prior to the addition of enzyme to test the effectiveness of the inhibitor against cPLA. As with any thiol assay, the presence of free thiols in the buffer or enzyme solutions, or the use of a colored inhibitor can increase the observed absorbance. Thus, appropriate blanks should be run under each condition tested.

In order that the invention described herein may be more fully understood, the following examples are set forth. It should be understood that these examples are for illustrative purposes only and are not to be construed as limiting the scope of the invention in any manner.

Example 1:

Synthesis of 1-Hexadecyl-2-arachidonoylthio-2-deoxy-sn-glycero-3-phosphorylcholine The substrate, 1-Hexadecyl-2-arachidonoylthio-2-deoxy-sn-glycero-3-phosphorylchlorine, was synthesized according to the scheme shown in FIG. 1.

Preparation of (R)-(+)-(Tetrahydro-2-pyranyloxy)-glycidol 1. Tetrahydropyranylation was carried out according to the procedure of Miyashita et al. (J. Org. Chem. 42:3772–2774 (1977)). A solution of (R)-glycidol (25 g, 338 mmol), dihydropyran (42.5 g [46 ml], 506 mmol), and pyridinium-p-toluenesulfonate (12.7 g, 51 mmol) in dry methylene chloride (200 ml) was stirred for 5 hr at room temperature. The solution was then washed three times with half-saturated brine. The brine was extracted once with chloroform, and the extract added back to the methylene chloride solution. The organic phase was then dried over $Na_2SO_4$ and the solvent was removed in vacuo. Vacuum distillation yielded 26.6 g (50 % yield) of compound 1 (shown in FIG. 1).

Preparation of 3-hexadecyl-1-(tetrahydro-2-pyranyloxy)-sn-glycerol 2. 1-Hexadecanol (42.5 g, 175 mmol) was added to a suspension of sodium hydride (7 g, 175 mmol) in 200 ml of dry tetrahydrofuran. After the heterogenous mixture was stirred for 1 hr at 60° C., compound 1 (18.5 g, 17 mmol) in 50 ml of anhydrous tetrahydrofuran was added and the resulting mixture was refluxed overnight. The reaction was cooled in an ice bath and 2N HCl was added slowly to neutralize the solution. The mixture was then diluted with water and extracted twice with ether. After drying the combined extracts over anhydrous sodium sulfate, the solvent was removed under reduced pressure. The resulting residue was purified by flash chromatography on silica gel with petroleum ether/ethyl acetate (95:5) as the eluting solvent to give compound of FIG. 1 as a yellowish liquid (15 g, 32%). $R_f$ 0.42 in petroleum ether/ethyl acetate (8:2). $^1$H NMR (CDCl$_3$) δ0.879 (t, 3H), 1.254 (s, 26H), 1.549 (br, 4H), 1.732 (m, 2H), 3.468 (m, 4H), 3.524 (t, 2H), 3.901 (t, 2H), 4.191 (q, 2H), 4.581 (br s, 1 H), 4. 897 (br, 1 H).

Preparation of 3-hexadecyl-2-(p-nitrobenzenesulfonyl)-1-sn-glycerol 3. A solution of compound 2 (9.5 g, 23.7 mmol), p-nitrobezenesulfonyl chloride (6.3 g, 28.5 mmol), and 4-dimethylamino-pyridine (3.5 g, 28.5 mmol) in 200 ml of anhydrous dichloromethane was stirred at room temperature for 24 hr. The reaction mixture was then washed twice with water, the organic layer dried over sodium sulfate, and the solvent removed in vacuo. The residual oil was flash chromatographed on silica gel and eluted with petroleum ether/ethyl acetate (95:5) to give a yellow oil (10.9, 78%). $R_1$ 0.38 in petroleum ether/ethyl acetate (9:1) and 0.81 in petroleum ether/ethyl acetate (8:2). $^1$H NMR (CDCl$_3$) 6 0.879 (t, 3H), 1.256 (s, 26H), 1.491 (m, 4H), 1.702 (m, 2H), 3.357 (t, 2H), 3.486 (m, 1H), 3.624 (m, 4H), 3.739 (m, 1H), 3.889 (m, 2H), 4.646 (br, 1H), 4.875 (m, 1H), 8.159 (d, 2H), 8.345 (d, 2H).

Preparation of 1-hexadecyl-2-acetylthio-2-deoxy-3-(tetrahydro-2-pyranyloxy)-sn-glycerol 4. A mixture of compound 3 (8.0 g, 13.7 mmol) and potassium thioacetate (2.4 g, 20.5 mmol) in 150 ml of anhydrous acetonitrile was stirred at 50° C. for 8 hr. After the reaction mixture was filtered, the filtrate was concentrated, applied to a flash silica gel column, and eluted with hexanes/ethyl acetate (100:3) to give a yellowish oil (3.8 g, 60%). $R_f$ 0.49 in petroleum ether/ethyl acetate (95:5). $^1$H NMR (CDCl$_3$) 60.880 (t, 3H), 1.255 (s, 26H), 1.549 (m, 4H), 1.741 (m, 2H), 2.335 (s, 3H), 3.438 (t, 2H), 3.525 (m, 3H), 3.609 (m, 3H), 3.850–3.952 (m, 3H), 4.641 (br, 1 H).

Preparation of 1-hexadecyl-2-thio-2-deoxy-3-(tetrahydro-2-pyranyloxy)-sn-glycerol 5. Lithium borohydride (6.5 mmol) was added to a solution of compound 4 (2.0 g, 4.32 mmol) in 50 ml of anhydrous tetrahydrofuran. The reaction suspension was refluxed and methanol (0.8 ml) was added dropwise over a period of 20 min. After stirring for another 20 min at room temperature, the reaction mixed was cooled in an ice bath and excess hydride was decomposed by the cautious addition of 1N HCl. The suspension was acidified with 6N HCl and extracted twice with ether. The organic layers were combined, washed with 5% NaHCO$_3$, and then water. The ether layer was dried over anhydrous Na$_2$SO$_4$ and the solvent was removed in vacuo. The crude product was purified by flash chromatography on silica gel with petroleum ether/ethyl acetate (100:1.5) as the eluting solvent to give thiol compound 5 (1.35 g, 75%) as a yellowish liquid. $R_f$ 0.5 in petroleum ether/ethyl acetate (95:5).

Preparation of 1-hexadecyl-2-arachidonoylthio-2-deoxy-3-(tetrahydro-2-pyranyloxy)-sn-glycerol [6]. A solution of arachidonic acid (1.0 g, 3.12 mmol) and 1,1'-carbonyldiimidazole (0.533 g, 3.28 mmol) in 50 ml of chloroform was stirred at room temperature for 2 hr. A solution of thiol compound 5 (1.3 g, 3.13 mmol) in 100 ml of chloroform containing 0.5 ml of triethylamine was added and the solution stirred for 24 hr at room temperature. The reaction was monitored by TLC in petroleum ether/ethyl acetate (95:5) by following the disappearance of the starting material. After the reaction was complete, the reaction mixture was washed first with 0.5N HCl, then with water, and finally with 5% $NaHCO_3$. The organic layer was dried over sodium sulfate and the chloroform evaporated under reduced pressure. The resulting residue was purified by flash chromatography on silica gel with petroleum ether/ethyl acetate (100:1) as the eluting solvent to give a yellowish oil (2.0 g, 91%). $R_f$ 0.53 in petroleum ether/ethyl acetate (95:5). $^1$H NMR ($CDCl_3$) δ 0.880 (t, 6H), 1.254 (s, 32H), 1.544 (m, 6H), 1.737 (m, 2H), 2.099 (m, 4H), 2.562 (t, 2H), 2.828 (m, 6H), 3.454 (t, 2H), 3.523 (m, 3H), 3.599 (m, 3H), 3.835–3.942 (m, 3H), 4.639 (br s, 1H), 5.318 (m, 8H).

Preparation of 1-hexadecyl-2-arachidonoylthio-2-deoxy-sn-glycero [7]. A mixture of compound 6 (1.8 g, 2.56 mmol) and pyridium p-toluenesulfonate (0.13 g, 0.5 mmol) in 20 ml of ethanol was stirred at 55° C. for 1.5 hr. After the reaction was completed, the ethanol was removed under vacuum. The residue was dissolved in 100 ml of chloroform and washed with water. The organic solution was dried over anhydrous $MgSO_4$ and evaporated in vacuo. A yellowish oil was obtained which showed a major spot on TLC. This liquid was used directly in next step without further purification.

Preparation of 1-hexadecyl -2-arachidonoylthio-2-deoxy-sn-glycero-3 -phosphorylcholine [8]. A solution of the crude compound 7 from the previous step and freshly distilled $POCl_3$ (0.5 g, 3.2 mmol) in 50 ml of dry chloroform containing 0.3 ml of dry pyridine (3.75 mmol) was stirred at room temperature for 6 hr. After the starting material disappeared, choline p-toluenesulfonate (1.2 g, 3.2 mmol) and 1 ml of dry pyridine were added and the solution was stirred at room temperature for an additional 24 hr. The reaction mixture was washed with water; methanol was added to break up the resulting emulsion. The organic solution was mixed with 50 ml Rexyn 1–300 which had been prewashed with methanol. The solvent was separated, the Rexyn washed three times with chloroform, and the solution was dried over anhydrous sodium sulfate. The crude product was concentrated and purified by flash chromatography on silica gel with chloroform/methanol/water (65:25:3) as eluting solvent. The yield of compound 8 was 796 mg (40% from compound 7). $^1$H NMR ($CDCl_3$) 6 0.889 (t, 6H), 1.254 (s, 32H), 1.481 (m, 2H), 1.633 (m, 2H), 2.085 (m, 4H), 2.558 (t, 2H), 2.832 (m, 8H), 3.414(s, 9H), 3.611 (t, 2H), 3.851 (m, 2H), 3.962 (m, 4. 95 (m, 2H), 5. 98 (m, 8H). HRMS (FAB, MH$^+$) Calcd. for $C_{44}H_{83}NPSO_6$: 784.5679. Found: 784.5711.

The foregoing example illustrates the preparation of a preferred thiosubstrate hereof. In like manner, other thio-substrates of the present invention are prepared using the appropriate starting materials.

For example, by employing alcohols other than hexadecanol in the preparation of 2, other R substituted substrates hereof are prepared as illustrated:

| alcohol | R substituent |
| --- | --- |
| hexanol | 1-hexyl |

-continued

| alcohol | R substituent |
| --- | --- |
| octanol | 1-octyl |
| decanol | 1-decyl |
| dodecanol | 1-dodecyl |
| tetradecanol | 1-tetradecyl. |

Further, alternative R' substituted substrates hereof are prepared by using alternative acids in the preparation of 6, as illustrated:

| acid | R' substituent |
| --- | --- |
| hexadecene-1-carboxylic acid | 2-hexadecenoyl |
| octadecene-1-carboxylic acid | 2-octadecenoyl |
| docosene-1-carboxylic acid | 2-docosenoyl |
| including polyene analogues thereof. | |

Further, and in combination with the foregoing R and R' alternatives, alternative R" substituted substrates hereof are prepared by modification of the reaction for preparing 8, as illustrated:

| tosylate | R" substituent |
| --- | --- |
| ethanolamine tosylate | 3-phosphorylethanolamine |
| inositol tosylate | 3-phosphorylinositol |
| glycerol tosylate | 3-phosphorylglycerol |
| methanol tosylate | 3-phosphorylmethanol |
| propanol tosylate | 3-phosphorylpropanol |
| sec-butanol tosylate | 3-phosphoryl-sec-butanol. |

Example 2

Microtiterplate Assay for cPLA$_2$ Using Substrate of 1-hexadecyl-2-arachidonoylthio-2-deoxy-sn-glycero-3 -phosphorylcholine The enzyme activity of CPLA$_2$ was assayed using a ThioPC/Triton X-100 substrate solution. An appropriate volume of ThioPC in chloroform solution was evaporated to dryness under a stream of $N_2$. Triton X-100 (8 mM) in 2× assay buffer (160 mM HEPES, pH 7.4, 300 mM NaCl, 20 mM CaC$_2$, 2 mg/ml BSA) was added to the dried lipid in one-half the desired final volume to give a 2-fold concentrated substrate solution. This solution was bath sonicated 1 min to loosen dried ThioPC from the walls of the vial and then probe sonicated On ice, 20 sec on, 20 sec off for 3 min. The solution was then warmed to 40° C. and warm glycerol equivalent to 30% of the final volume was added. The solution was then brought to the desired final volume with deionized H$_2$O. The final assay contained 2 mM ThioPC, 4 mM Triton! X-100 and 30% glycerol in 80 mM HEPES, pH 7.4, 150 mM NaCl, 10 mM CaCl$_2$ and 1 mg/ml BSA.

The substrate was then aliquotted, in 200 μl increments, into the wells of a 96-well plate and equilibrated for 5 min at 37° C. To initiate the reaction, 500 ng cPLA$_2$ (purified, recombinant human), in a 5 μl volume of 1× assay buffer, was added to the wells, the plate was shaken 20 seconds on high to mix, and then incubated for 60 min at 37° C. The enzyme was prepared using known recombinant methods (Sharp, et al., supra). For blanks, buffer rather than enzyme was added to some wells.

After 60 min, 10 µl of a 25 mM DTNB/475 mM EGTA mixture was added to all substrate containing wells to quench the reaction and initiate the color development. The DTNB/EGTA mixture was prepared just prior to use by combining equal volumes of 50 mM DTNB in 0.5M Tris, pH 7.4 and 950 mM EGTA, pH 7.2. After adding the DTNB/EGTA, the plate was once again shaken 20 sec on high and allowed to incubate for an additional 3 min to give the DTNB chromophore time to fully develop prior to reading the plate. The absorbance was measured using a dual wavelength option (405 nm –620 nm) to correct for light scattering. The results obtained with this dual wavelength option were similar to those obtained using a single wavelength (405 nm) but were more reproducible. The average absorbance of the blanks was subtracted from that of the enzyme containing wells to correct for the absorbance due to the substrate, DTNB, and EGTA. The difference in absorbance was used to calculate enzyme activity. The data was reported ± the standard deviation. Specific activity was calculated using $\epsilon_{405}$ for DTNB of 12,800 M$^{-1}$cm$^{-1}$ (Yu et al supra) and a path length of 0.47 cm for 215 µl final total volume. The path length in these plates is dependent on the assay volume and was calculated by measuring the absorbance of several concentrations of bromothymol blue, where the path length equals the absorbance observed on the plate reader divided by the absorbance observed for the same solution in the spectrophotometer in 1 cm cuvettes. FIG. 3 shows enzyme activity measured as a function of time. A short burst of activity was observed in the firsts 5 minutes followed by a more linear phase from 5 to 60 minutes. The generally linear nature of the time course is a distinct advantage of the substrate form over other substrates, such as vesicles which result in a burst of activity with leveling off within 5 to 10 minutes.

In like manner the other alternative substrates hereof, prepared as illustrated above are employed in the assay for cPLA$_2$ as described in Example 2.

The foregoing description details specific methods that can be employed to practice the present invention. Having detailed specific methods for the synthesis of thiosubstrates and the use of these substrates in spectrophotometric assays, and having provided specific model systems for such synthesis and use, those skilled in the art will well enough know how to devise alternative reliable methods for arriving at the same information and for extending this information to other equivalent substrates and assays. Thus, however detailed the foregoing may appear in text, it should not be construed as limiting the overall scope hereof; rather, the ambit of the present invention is to be governed only by the lawful construction of the appended claims.

What is claimed is:

1. A compound useful as a substrate in cytosolic phospholipase A$_2$ assays having the formula:

$$\begin{array}{c} H_2C-OR \quad\quad O \\ | \quad\quad\quad\quad || \\ HC-S-\!\!-\!\!-C-R' \\ | \quad\quad O \\ | \quad\quad || \\ H_2C-OP-R'' \\ | \\ O^{(-)} \end{array}$$

wherein R is an alkyl or alkenyl group having from about 6 to about 18 carbon atoms, R' is an alkenyl group having at least one double bond and having from about 16 to about 22 carbon atoms, and R" is a polar group selected from the group consisting of oxy radicals of choline, ethanolamine, inositol, serine, glycerol, and alkanols having from 1 to 4 carbons.

2. The compound of claim 1 wherein R' is the alkenyl component of arachidonic acid, having the formula:

—(CH$_2$)$_2$(CH$_2$CH=CH)$_4$(CH$_2$)$_4$CH$_3$.

3. The compound of claim 2 wherein R is hexadecyl.

4. The compound of claim 3 wherein R" is the oxy radical of choline.

5. The compound of claim 2 wherein R" is selected from the group consisting of oxy radicals of choline, ethanolamine, inositol, serine, and glycerol.

6. A method of measuring the activity of cytosolic phospholipase A$_2$ enzyme comprising:

a) incubating said enzyme with a substrate solution to allow an enzyme/substrate reaction, said substrate solution comprising a cytosolic phospholipase A$_2$ substrate having a formula:

$$\begin{array}{c} H_2C-OR \quad\quad O \\ | \quad\quad\quad\quad || \\ HC-S-\!\!-\!\!-C-R' \\ | \quad\quad O \\ | \quad\quad || \\ H_2C-OP-R'' \\ | \\ O^{(-)} \end{array}$$

wherein R is an alkyl or alkenyl group having from about 6 to about 18 carbon atoms, R' is an alkenyl group having at least one double bond and having from about 16 to about 22 carbon atoms, and R" is a polar group selected from the group consisting of oxy radicals of choline, ethanolamine, inositol, serine, glycerol, and alkanols having from 1 to 4 carbons;

(b) adding an enzyme quenching reagent to said enzyme/substrate solution;

c) adding to thiol-sensitive reagent to said solution to produce a chromophore; and d) measuring the absorbance of said solution by spectrophotometric means.

7. The method of claim 6 wherein R' is the alkenyl component of arachidonic acid, having the formula:

—(CH$_2$)$_2$(CH$_2$CH=CH)$_4$(CH$_2$)CH$_3$.

8. The method of claim 7 wherein R is hexadecyl and R" is the oxy radical of choline.

9. The method of claim 7 wherein said substrate solution comprises about 1–3 mM substrate and wherein the amount of said enzyme is between 0.05–1.0 µg.

10. The method of claim 7 wherein said substrate solution further comprises glycerol, detergent, and calcium.

11. The method of claim 10 wherein said substrate solution contains about 25% to 75% glycerol.

12. The method of claim 10 wherein said detergent is Triton X-100 and is present at a concentration of about 1 to 5 mM.

13. The method of claim 10 wherein said calcium is present at a concentration of greater than 1 mM.

14. The method of claim 6 wherein said thiol-sensitive reagent is 5,5'-dithiobis(2-nitrobenzoic acid).

15. A method of measuring the effectiveness of phospholipase A$_2$ enzyme inhibitor comprising:

a) adding said enzyme inhibitor to a substrate solution, and substrate solution comprising a cytosolic phospholipase $A_2$ substrate having the formula:

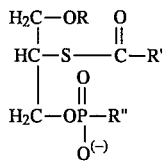

wherein R is an alkyl or alkenyl group having from about 6 to about 18 carbon atoms, R' is an alkenyl group having a least one double bond and having from about 16 to about 22 carbon atoms, and R" is a polar group selected from the group consisting of oxy radicals of choline, ethanolamine, inositol, serine, glycerol, and alkanols having from 1 to 4 carbons;

b) incubating a cytosolic phospholipase $A_2$ enzyme with said solution;

c) adding an enzyme quenching reagent to said solution;

d) adding a thiol-sensitive reagent to said solution; and e) measuring the absorbance of said solution by spectrophotometric means.

16. The method of claim 15 wherein R' is the alkenyl component of arachidonic acid, having the formula:

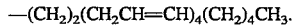

17. The method of claim 16 wherein R is hexadecyl and R" is the oxy radical of choline.

18. The method of claim 17 wherein said substrate solution comprises about 1–3 mM substrate and wherein the amount of said enzyme is between 0.05–1.0 µg.

19. The method of claim 17 wherein said substrate solution further comprises glycerol, detergent, and calcium.

20. The method of claim 19 wherein said substrate solution contains about 25% to 75% glycerol.

21. The method of claim 19 wherein said detergent is Triton X-100 and is present at a concentration of about 3 to 5 mM.

22. The method of claim 19 wherein said calcium is present at a concentration of greater than 1 mM.

23. The method of claim 15 wherein said thiol-sensitive reagent is 5,5'-dithiobis(2-nitrobenzoic acid).

* * * * *

UNITED STATES PATENT AND TRADEMARK OFFICE
CERTIFICATE OF CORRECTION

PATENT NO. : 5,464,754      Page 1 of 2

DATED : November 7, 1995

INVENTOR(S) : DENNIS et al.

It is certified that error appears in the above-indentified patent and that said Letters Patent is hereby corrected as shown below:

On the Title page under OTHER PUBLICATIONS, at Trautwein, et al., delete "Pflëgers" and insert therefor --Pflügers--;

under OTHER PUBLICATIONS, at Sharp et al., delete "$Ga^{2+}$" and insert therefor --$Ca^{2+}$--;

under OTHER PUBLICATIONS, at Reynolds, et al., delete "Biochemica" and insert therefor --Biochimica-- ;

under ABSTRACT [57], line 6, delete "alkenyl" and insert therefor --alkyl--.

Column 2, line 11, immediately preceding "alkenyl-ether" insert --alkyl-ether or--.

Column 2, line 12, immediately preceding "alkenylthioester" delete --unsaturated--.

Column 4, line 22, immediately following "solubilize" delete --!--.

Column 5, line 52, delete "phosphorylchlorine" and insert therefor --phosphorylcholine--.

Column 5, line 57, immediately following "solution" delete --.--.

Column 6, line 31, immediately preceding "0.879" delete "6" and insert therefor --δ--.

Column 6, line 43, immediately preceding "0.880" delete "6" and insert therefor --δ--.

UNITED STATES PATENT AND TRADEMARK OFFICE
CERTIFICATE OF CORRECTION

PATENT NO. : 5,464,754

DATED : November 7, 1995

INVENTOR(S) : DENNIS et al.

It is certified that error appears in the above-indentified patent and that said Letters Patent is hereby corrected as shown below:

Column 7, line 48, immediately preceding "0.889" delete "6" and insert therefor --δ--.

Column 7, line 51, delete "(m,4.95 (m,2H),5.98" and insert therefor --(m,3H), 4.395 (m,2H), 5.398--.

Column 8, line 48, delete "$CaC_2$" and insert therefor --$CaCl_2$--.

Column 8, line 52, delete "sonicated On" and insert therefor --sonicated on--.

Column 8, line 57, immediately following "Triton" delete --!--.

Column 9, line 20, delete "$M^-cm^{-1}$" and insert therefor --$M^{-1}cm^{-1}$--.

Signed and Sealed this

Twenty-ninth Day of October 1996

Attest:

BRUCE LEHMAN

*Attesting Officer*  *Commissioner of Patents and Trademarks*